United States Patent [19]

Mirviss

[11] Patent Number: 4,613,677
[45] Date of Patent: Sep. 23, 1986

[54] ONE-STEP HYDROGENATION/ESTERIFICATION OF BENZYLOXY PHENOXY PROPANOIC ACID

[75] Inventor: Stanley B. Mirviss, Stamford, Conn.

[73] Assignee: Stauffer Chemical Company, Westport, Conn.

[21] Appl. No.: 804,963

[22] Filed: Dec. 5, 1985

[51] Int. Cl.⁴ .............................................. C07C 69/76
[52] U.S. Cl. ....................................................... 560/61
[58] Field of Search .......................................... 560/61

[56] References Cited

U.S. PATENT DOCUMENTS

| 3,717,669 | 2/1973 | Grant et al. | 560/61 |
| 3,759,950 | 9/1973 | Grant et al. | 560/61 |
| 3,795,691 | 3/1974 | Douglas et al. | 560/61 |

FOREIGN PATENT DOCUMENTS 7149240  9/1982  Japan ..................................... 560/61

Primary Examiner—Paul J. Killos
Attorney, Agent, or Firm—Vivienne T. White

[57] ABSTRACT

The invention is directed to the one-step hydrogenation/esterification of arylmethyleneoxyaryloxy alkanoic acids to produce (hydroxyphenoxy) carboxylates. The process comprises the hydrogenation and esterification of the aryloxy alkanoic acid in the presence of a palladium hydrogenation catalyst and an acidic esterification catalyst preferably utilizing the alcohol for the esterification as the hydrogenation solvent. The acid serves the dual role of hydrogenation promoter and esterification catalyst.

13 Claims, No Drawings

ONE-STEP HYDROGENATION/ESTERIFICATION OF BENZYLOXY PHENOXY PROPANOIC ACID

BACKGROUND OF THE INVENTION

Related Art

The present invention relates to the process for the preparation of (hydroxyphenoxy)-carboxylates. These compounds are suitable intermediates for the synthesis of biological and in particular herbicidally active ingredients such as Fusilade and Dowco 453.

Various methods of preparing (hydroxyphenoxy)-carboxylates are known in the art. For instance, U.S. Pat. No. 4,489,207 discloses a process for the production of 2-(hydroxyphenoxy)-carboxylates. In the processes discussed therein as prior art there is described a reaction of hydroquinone with 2-halo carboxylate in an alcoholic solution in the presence of sodium alcoholate. Also disclosed is the reaction of hydroquinone with ethyl chloroacetates in the presence of boron trifluoride. In addition there is disclosed the alkylation of hydroquinone in the form of its disodium salt with 2-bromocarboxylates in certain water-soluble organic solvents.

The process of the invention disclosed in U.S. Pat. No. 4,489,207 is the reaction of a dihydroxybenzene compound with a 2-halo-fatty acid ester in the presence of calcium hydroxide in dimethyl sulfoxide (DMSO) at from 0° C.–100° C.

SUMMARY OF THE INVENTION

In the instant application (hydroxyphenoxy) carboxylates are prepared from arylmethyleneoxyaryloxy alkanoic acids of the formula $R'ArOR''CO_2H$ such as benzyloxyphenoxy alkyl carboxylic acids by hydrogenating in the presence of a palladium catalyst and an acidic esterification catalyst, preferably using an alcohol for the esterification and as the solvent for the hydrogenation. The acid serves the dual role of hydrogenation promoter and esterification catalyst. In the practice of the invention the R' blocking group is hydrogenated using a palladium catalyst in the presence of an acidic promoter such as a protonic acid.

DETAILED DESCRIPTION OF THE INVENTION

In the preparation of the intermediary product of this invention, it is necessary to remove a phenolic blocking group of the carboxylic acid and then carry out an esterification of the deblocked carboxylic acid as the next reaction step. The esterification is promoted by an acidic catalyst. This invention is characterized by a palladium catalyzed hydrogenation, in the presence of an acidic esterification catalyst, of an aryloxy alkanoic acid using the alcohol for the esterification as the hydrogenation solvent.

The starting material for the reaction is preferably an aryloxy alkanoic acid, desirably a benzyloxyphenoxycarboxylic acid (arylmethyleneoxyaryloxyalkanoic acid). The aryloxyalkanoic acid reactants of the process of this invention are preferably represented by the formula $R'Ar OR''CO_2H$ wherein R' can be benzyloxy (ortho, meta, para); Ar is phenyl or naphthyl; R'' is an alkyl group of a straight chain alkanoic acid of from $C_2$ to $C_5$ or of a branched chain alkanoic acid of from $C_3$ to $C_6$ attached at the alpha, beta, or other carbon atom of the acid moiety, and at the oxygen of the Ar group at the ortho, meta or para position. The aryloxyalkanoic acid reactants of the invention (specifically arylmethyleneoxyaryloxyalkanoic acids) can be prepared as disclosed in copending U.S. Application Ser. No. 786,556, filed Oct. 11, 1985 by reacting a phenol with a haloalkanoic acid in the presence of a base and a solvent (alcohol). The aryloxyalkanoic acid product is recovered by acidification of the reaction mixture in the presence of the solvent (which is also the esterification alcohol) and then separation therefrom. The methods disclosed in the "Related Art" section of copending application Ser. No. 786,556, filed October 11, 1985, incorporated herein by reference also describes additional methods for preparing aryloxyalkanoic acids, as for instance, reacting hydroquinone monobenzyl ether, alphachloropropionic acid in ethanol with sodium hydroxide.

In the process of the instant invention the aryloxyalkanoic acid desirably benzyloxyphenoxy carboxylic acid is reacted with an alcohol and hydrogen in the presence of an acidic esterification catalyst and a hydrogenation catalyst to produce the hydroxyphenoxycarboxylate product. The acidic esterification catalyst has the additional role of activating the hydrogenation catalyst. The following equation is descriptive of the process of the invention.

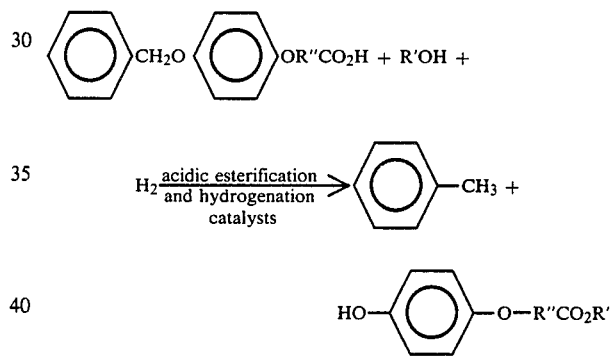

Acidic esterification catalysts suitably used in the process of the invention are mineral acids or strong organic acids such as sulfonic acids or polymeric sulfonic acids and particularly polymeric sulfonic acids such as ion exchange resins in their acidic form such as the Amberlites ® brands or the Dowex ® brands of resins. Particularly useful examples include Dowex ® HCR-S, ACR-W2, AGR or MSC-1 brand resins or the Amberlyst 15, XN-010, 200, 252, IR-118(H) or IR-130C brand resins.

Solvents suitable for use in practicing the invention are alcohols which correspond to the specific esterification product being formed and optionally other aromatic and aliphatic solvents such as toluene, carbon tetrachloride, benzene, diethyl ether, dimethyl sulfoxide, tetrahydrofluron, heptane, cyclohexane and the like. Generally alcohols of from $C_1$ to $C_6$ are desirable for practicing the invention and particularly the alcohol corresponding to the ester being made. It is preferred that the alcohol be dry before use. In the case of an alcohol with more than one carbon atom, a water azeotroping agent may be included, such as benzene, carbon tetrachloride, heptane, and the like. When methanol is used, a large excess of alcohol is required, however, an excess is not necessary when longer chain length alcohols are used with a water azeotroping agent. A suitable excess of methanol is from 2-30 times the stoichiometric amount.

Hydrogenation catalysts for practicing the invention are Group VIII noble metals, particularly palladium. The metal may be used as the free metal but is preferably used in powder form or supported on an inert carrier such as charcoal, $BaSO_4$, $CaCO_3$, $Al_2O_3$, $SiO_2$, and the like. Generally in the practice of the invention from about 0.1 wt. % to about 15 wt. % of the hydrogenation catalyst is used based on the amount of aryloxyalkanoic acid used. The cataylst when utilized is desirably supported on from 1-20 wt. % of the inert carrier support, such as desirably a 5 or 10 wt. % palladium on charcoal.

The reaction process can be conducted at a temperature of from about 25° C. to reflux. Generally it is preferable to conduct the reaction at reflux temperatures. The reactor can be sparged with nitrogen or other inert gases or hydrogen before use to flush out all oxygen. The reaction is conducted with some agitation, e.g., stirring, to provide good contact between the catalyst and the hydrogen. It is preferable that the reaction be conducted in an anhydrous environment to facilitate esterification. The process of the invention may be carried out in a continuous manner with either catalyst recycled after filtration (to remove the catalyst from the reaction product which is continuously removed from the reaction vessel) or with small amounts of fresh catalyst continuously added to the reaction.

The invention is particularly directed to the preparation of methyl 2-(4-hydroxyphenoxy)propionate of the formula

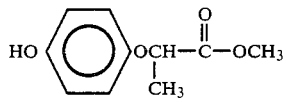

The following Examples are descriptive of the invention.

EXAMPLE 1

A 22 liter round bottom flask was charged with 3.5 kg. of para-benzyloxyphenoxy-2-propionic acid (12.87 moles), 12 liters of methyl alcohol (predried) and 380 g. of Amberlyst 15 (Rohm and Haas) ion exchange resin. The flask was swept with nitrogen and then hydrogen. Then 200 g. of 10% palladium on charcoal catalyst was added under a flow of hydrogen with vigorous stirring as the temperature was slowly raised to reflux at atmospheric pressure. The reaction mixture was analyzed after 8 hrs. and the hydrogenation was found to be complete, i.e., no benzyloxy group left. The esterification, however, was only 90% complete. The refluxing was continued for another 12 hrs. and the reaction then sampled and found to be 98% complete (liquid chromatography analysis). The reaction mixture was then filtered to remove the catalyst. The filtrate was stripped at 10 mm. Hg vacuum at 25°-85° C. to remove all water and methanol. The remaining oily liquid weighed 2185 g. for an 89% yield. The purity by liquid chromatographic analysis was 98%.

EXAMPLE 2

Another experiment was conducted which was identical to the above except that the hydrogenation-esterification was carried out completely at reflux. The hydrogenation part was done in 3 hrs. and the esterification was complete in an additional 4 hrs. The product purity was 99% and the yield was over 90%.

What is claimed is:

1. A process for preparing (hydroxyphenoxy) carboxylates from arylmethyleneoxyaryloxyalkanoic acids comprising reacting the acid with an alcohol and hydrogen in the presence of an acidic esterification catalyst and an hydrogenation catalyst.

2. The process of claim 1 wherein the catalyst are filtered to recover the product.

3. The process of claim 1 wherein the alcohol is a $C_1$ to $C_6$ alcohol.

4. The method of claim 3 wherein the alcohol is methanol.

5. The process of claim 3 wherein the alcohol is ethanol.

6. The process of claim 1 wherein the alcohol is pre-dried prior to use.

7. The process of claim 1 wherein a water azeotroping agent is used.

8. The process of claim 7 wherein the water azeotroping agent is benzene.

9. The process of claim 7 wherein the azeotroping agent is toluene.

10. The process of claim 4 wherein the methanol is used in from about 2-20 times in excess of stoichiometric amounts.

11. The process of claim 1 wherein the alcohol is the solvent for the hydrogenation reaction.

12. The process of claim 1 wherein the arylmethylenearyloxyalkanoic acid is benzyloxyphenoxypropionic acid.

13. The process of claim 2 wherein the recovered catalyst is recycled to a subsequent reaction.

* * * * *